US006482596B1

(12) United States Patent
Ueda et al.

(10) Patent No.: US 6,482,596 B1
(45) Date of Patent: *Nov. 19, 2002

(54) METHOD FOR MEASURING ANTIGEN CONCENTRATION

(75) Inventors: Hiroshi Ueda, Tokyo (JP); Teruyuki Nagamune, Saitama (JP); Hajime Nishimura, Kanagawa (JP); Izumi Kumagai, Miyagi (JP); Kouhei Tsumoto, Miyagi (JP); Walter C. Mahoney, Benicia, CA (US); Greg Winter, Cambridge (GB); Paula A. Schueler, Benicia, CA (US)

(73) Assignee: Roche Diagnostics Corporation, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/313,350

(22) Filed: May 18, 1999

Related U.S. Application Data

(63) Continuation of application No. 08/663,922, filed on Jun. 14, 1996, now Pat. No. 5,981,199.

(51) Int. Cl.[7] ................ G01N 33/53; G01N 33/543; G01N 33/573

(52) U.S. Cl. ................ 435/7.1; 436/512; 436/546; 436/172; 435/7.5; 435/7.9; 435/7.92; 435/7.94

(58) Field of Search ................ 436/512, 544, 436/546, 172; 435/4, 7.1, 7.5, 7.9, 7.92, 7.94, 21; 530/413

(56) References Cited

U.S. PATENT DOCUMENTS

| 4,859,609 A | 8/1989 | Dull et al. |
| 5,030,576 A | 7/1991 | Dull et al. |
| 5,196,510 A | 3/1993 | Rodwell et al. |
| 5,424,192 A | * 6/1995 | Thompson et al. |
| 5,639,660 A | 6/1997 | Kinet et al. |
| 5,948,894 A | * 9/1999 | Berry et al. |

FOREIGN PATENT DOCUMENTS

JP 5-184386 7/1993

OTHER PUBLICATIONS

Database Caplus, DN 122:26912; Szollosi, J. et al. Cytometry (1998), 34(4), 159–179, Apr. 1998.*

Database Caplus, DN 129:327783; Tron L. Mobility Proximity Biol. Membr. (Jan. 1994), 1–47 Publisher: CRC, Boca Raton, Fla.*

Database Caplus, DN : 121:106236; Mallender et al. Biochemistry (1994), 33(33), 10100–8, Feb. 1994.*

(List continued on next page.)

Primary Examiner—Michael Borin
(74) Attorney, Agent, or Firm—Wenderoth, Lind & Ponack, L.L.P.

(57) ABSTRACT

This invention provides a method for measuring an antigen concentration in a sample, which comprises: preparing VH-domain polypeptide and VL-domain polypeptide of an antibody specific to the antigen; labeling one of the polypeptides with a reporter molecule to form labeled polypeptides, and immobilizing the other polypeptide onto solid-phase to form immobilized polypeptides; contacting the antigen-containing sample and the labeled polypeptides with the solid-phase; and measuring the reporter molecule of the labeled polypeptides bound to the immobilized polypeptides. The present invention permits simpler and quicker sandwich ELISA for measurements of an antigen concentration in high sensitivity.

10 Claims, 5 Drawing Sheets

OTHER PUBLICATIONS

Anthony, J. et al., (1992) "Production of stable anti–digoxin Fv in *Escherichia Coli*" *Mol. Immunol.* 29(10):1237–1247.

Better, M. et al., (May 20, 1988) "*Escherichia coli* secretion of an active chimeric antibody fragment" *Science* 240:1041–1043.

Bird, R.E. et al., (Oct. 21, 1988) "Single–chain antigen binding proteins" *Science* 242:423–426.

Brinkmann, B. K. et al., "Recombinant immunotoxins containing the $V_H$ or $V_L$ domain of monoclonal antibody B3 fused to Pseudomonas exotoxin" *J. Immunol.* 150(7):2774–2782 (1993).

Chothia, C. et al., (1985) "Domain association in immunoglobulin molecules. The packing of variable domains" *J. Mol. Biol.* 186(3):651–663.

D'Andrea, A.D. et al. (1989) "Expression cloning of the murine erythropoietin receptor" *Cell* 57:277–285.

Davies, J. et al., (1994) "'Camelising' human antibody fragments: NMR studies on VH domains" *FEBS Letters* 339:285–290.

Figini, M. et al., (1994) In vitro assembly of repertoires of antibody chains on the surface of phage by renaturation. *J. Mol. Biol.* 239:68–78.

Gavish, M et al., (1977) "Comparison of the fine specificity of anti–dinitrophenyl–combining site composed of either $V_L$ dimer or $V_L$ and $V_H$ of protein 315" *Biochem.* 16(14):3154–3159.

Glockshuber, R. et al., (1990) "A comparison of strategies to stabilize immunoglobulin $F_v$–fragments" *Biochemistry* 29(6):1362–1367.

Hamel, P.A. et al., (Nov. 1, 1987) "Relative noncovalent association constant between immunoglobulin H and L chains is unrelated to their expression or antigen–binding activity" *J. Immunol.* 139(9):3012–3020.

Hamel, P.A. et al., (1984) "Structural basis for the preferential association of autologous immunoglobulin subunits: role of the J region of the light chain" *Mol. Immunol.* 21(4):277–283.

Hamel, P.A. et al., (1986) "The role of the $V_L$ and $V_H$–segments in the preferential reassociation of immunoglobulin subunits" *Mol. Immunol.* 23(5):503–510.

Hamers–Casterman, C. et al., (Jun. 3, 1993) "Naturally occurring antibodies devoid of light chains" *Nature* 363:446–448.

Hillier, L. et al., (1997) "WashU–NCI human EST project" Internet abstract located at http://www.ncbi.nlm.nih.gov visited on Oct. 26, 1999, 2 pages total ; (see also GenBank Accession No. AA478153.1).

Hochman, J. et al., (1976) "Folding and interaction of subunits at the antibody combining site" *Biochemistry* 15(12):2706–2710.

Holliger, P. et al., (1993) "Engineering bispecific antibodies" *Curr. Opin. Biotech.* 4:446–449.

Horne, C. et al., (Aug. 1982) "Noncovalent association of heavy and light chains of human immunoglobulins. III. Specific interactions between $V_H$ and $V_L$" *J. Immunol.* 129(2):660–664.

Huse, W. (1992) "Chapter 5: Combinatorial antibody expression libraries in filamentous phage" *Antibody Engineering, A practical guide,* Borrebaeck, C., ed., Freeman, W.H. & Co., New York, pp. 103–120.

Huston, J.S. et al., (Aug. 1988) "Protein engineering of antibody binding sites: recovery of specific activity in an anti–digoxin single–chain Fv analogue produced in *Escherichia coli*" *Proc. Natl. Acad. Sci. USA,* Biochemistry, 85:5879–5883.

Joh, T. et al., (1987) "Cloning and sequence analysis of cDNAs encoding mammalian mitochondrial malate dehydrogenase" *Biochemistry* 26(9):2515–2520.

Jones, S.S. et al., (Jul. 1, 1990) "Human erythropoietin receptor: cloning, expression, and biologic characterization" *Blood* 76(1):31–35.

Klein, M. et al., (1979) "Equilibrium and kinetic aspects of the interaction of isolated variable and constant domains of light chain with the Fd' fragment of immunoglobulin G" *Biochemistry* 18(8):1473–1481.

Kuramochi, S. et al., (1990) "Characterization of murine erythropoietin receptor genes" 216:567–575.

Lu, G. et al., (Feb. 21, 1997) "Importance of the dimerdimer interface for allosteric signal transduction and AMP cooperativity of pig kidney fructose–1,6–bisphosphatase. Site–specific mutagenesis studies of Glu–192 and Asp–187 residues on the 190's loop" *J. Biol. Chem.* 272(8):5076–5081.

Maekawa, W.D. et al., (Mar. 1993) "Detection and characterization of new genetic mutations in individuals heterozygous for lactate dehydrogenase–B(H) deficiency using DNA conformation polymorphism analysis and silver staining" *Hum. Genet.* 91(2):163–168.

Maenaka, K. et al., (1996) "A stable phage–display system using a phagemid vector: phage display of hen egg–white lysozyme (HEL), *Escherichia coli* alkaline, phosphatase, and anti–HEL monoclonal antibody, HyHEL–10" *Biochem. Biophys. Res. Comm.* 218(3):682–687.

Mallender, W.D. et al., (Mar. 8, 1996) "Comparative properties of the single chain antibody and Fv derivatives of mAB 4–4–20. Relationship between interdomain interactions and the high affinity for fluorescein ligand" *J. Biol. Chem.* 271(10):5338–5346.

Matthews, B.W. et al., (May 16–17, 1996) "Abstracts of the 8th annual meeting of the protein engineering society of Japan" *Protein Engineering* 9(9):811.

McCafferty, J. et al., (Dec. 6, 1990) "Phage antibodies filamentous phage displaying antibody variable domains" *Nature* 348(6301):552–554.

Mei, S. et al., (Aug. 25, 1991) "Vasoactive intestinal peptide hydrolysis by antibody light chains" *J. Biol. Chem.* 266(24):15571–15574.

Miyazaki, K. et al., (Jan. 1994) "Chemical modification and site–directed mutagenesis of Tyr36 of 3–isopropylmalate dehydrogenase from *Thermus thermophilus* HB8" *Protein Eng.* 7(1):99–102.

Muyldermans, S. et al., (1994) "Sequence and structure of $V_H$ domain from naturally occuring camel heavy chain immunoglobulins lacking light chains" *Protein Engineering* 7(9):1129–1135.

Parsons, H.L. et al., (1996) "Directing phage selections towards specific epitopes" *Protein Engineering* 9(11):1043–1049.

Plückthun, A. (Dec. 1992) "Mono and bivalent antibody fragments produced in *Escherichia Coli:* engineering, folding, and antigen binding" *Immulog. Rev.,* published by Munksgaard, (Denmark) No. 130:151–188.

Polymenis, M. and Stollar, D.B. (Mar. 1, 1995) "Domain interactions and antigen binding of recombinant antiZ–DNA antibody variable domains" *Journal of Immunology* 154(5):2198–2208.

Riechmann, L. et al., (1988) "Expression of an antibody Fv fragment in myeloma cells" *J. Mol. Biol.* 203:825–828.

Schmidt, T. G.M. et al., (1993) "The random peptide library–assisted engineering of a C–terminal affinity peptide, useful for the detection and purification of a functional Ig Fv fragment" *Protein Engineering* 6(1):109–122.

Smith–Gill, S.J. et al., (1987) "A three–dimensional model of an anti–lysozyme antibody" *J. Mol. Biol.* 194:713–724.

Smith–Gill, S.J. et al., (Dec. 15, 1987) "Contributions of immunoglobulin heavy and light chains to antibody specificity for lysozyme and two haptens" *J. Immunol.* 139(12):4135–4144.

Sun, M. et al., (Jan. 7, 1994) "Antigen recognition by an antibody light chain" *J. Biol. Chem.* 269(1):734–738.

Tang, P.M. et al., (Apr. 7, 1995) "A high affinity digoxin-binding protein displayed on M13 is functionally identical to the native protein" *J. Biol. Chem.* 270(14):7829–7835.

Truong, H.T. et al., (Nov. 1991) "Inactive and temperature-sensitive folding mutants generated by tryptophan substitutions in the membrane–bound D–lactate dehydrogenase of *Escherichia coli*" *Biochemistry* 30(44):10722–10729.

Tsumoto, K. et al., (Aug. 4, 1995) "Role of Tyr residues in the contact region of anti–lysozyme monoclonal antibody HyHEL–10 for antigen binding" *J. Biol. Chem.* 270(31):18551–18557.

Tyutyulkova, S. et al., (1994) "Selection of functional human immunoglobulin light chains from a phage–display library" *Appl. Biochem. Biotechnol.* 47:191–198.

Wagner, C.R. et al., (Sep. 1990) "Site directed mutagenesis: a tool for enzyme mechanism dissection" *Trends Biotechnol.* 8:263–270.

Ward, E.S. (1992) "Chapter 6: Expression and purification of antibody fragments using *Escherichia Coli* as a host" *Antibody engineering: A practical guide.* Borrebaeck, C.A.K. (ed.) W.H. Freeman & Co., New York., pp. 121–138.

Ward, E.S. et al., (Oct. 12, 1989) "Binding activities of a repertoire of single immunoglobulin variable domains secreted from *Escherichia coli*" *Nature* 341:544–546.

Wigley, D.B. et al., (Jan. 1992) "Structure of a ternary complex of an allosteric lactate dehydrogenase from *Bacillus stearothermophilus* at 2.5 Å resolution" *J. Mol. Biol.* 223(1):317–335.

Anthony et al., "Production of stable anti–digoxin Fv in *Escherichia coli*" *Mol. Immunol.* (1992) 29:1237–1247.

Better et al., "*Escherichia coli* secretion of an active chimeric antibody fragment" *Science* (1988) 240:1041–1043.

Bird et al., "Single–chain antigen binding proteins" *Science* (1988) 242:423–426.

Chothia et al., "Domain association in immunoglobulin molecules. The packing of variable domains" *J. Mol. Biol.* (1985) 186(3):651–663.

Davies et al., "'Camelising' human antibody fragments: NMR studies on VH domains" *FEBS Letters* (1994) 339:285–290.

Davies et al., "Antibody VH domains as small recognition units" *Bio/Technology* (1995) 13:475–479.

Glockshuber et al., "A comparison of strategies to stabilize immunoglobulin Fv–fragments" *Biochemistry* (1990) 29:1362–1367.

Hamel et al., "Relative noncovalent association constant between immunoglobulin H and L chains is unrelated to their expression or antigen–binding activity" *J. Immunol.* (1987) 139:3012–3020.

Hamel et al., "Structure basis for the preferential association of autologous immunoglobulin subunits: role of the J region of the light chain" *Mol. Immunol.* (1984) 21:277–283.

Hamel et al., "The role of the VL and VH–segments in the preferential reassociation of immunoglobulin subunits" *Mol. Immunol.* (1986) 23:503–510.

Hamers–Casterman et al., "Naturally occurring antibodies devoid of light chains" *Nature* (1993) 363:446–448.

Hochman et al., "Folding and interaction of subunits at the antibody combining site" *Biochemistry* (1976) 15:2706–2710.

Holliger et al., "Engineering bispecific antibodies" *Curr. Opin. Biotech.* (1993) 4:446–449.

Horne et al., "Noncovalent association of heavy and light chains of human immunoglobulins. III. Specific interactions between VH and VL" *J. Immunol.* (1982) 129:660–664.

Huston et al., "Protein engineering of antibody binding sites: recovery of specific activity in an anti–digoxin single–chain Fv analogue produced in *Escherichia coli*" *Proc. Natl. Acad. Sci. USA* (1988) 85:5879–5883.

Internet abstract of Hillier et al., "WashU–NCI human EST project" (1997) GenBank Accession No. AA478153.1 http://www.ncbi.nlm.nihgov/htbin–...ery?uid=2206787&form=6&db=n&Dopt=g/ (2 pages total).

Internet abstract of Lu et al., "Importance of the dimerdimer interface for allosteric signal transduction and AMP cooperativity of pig kidney fructose–1,6–bisphosphatase. Site–specific mutagenesis studies of Glu–192 and Asp–187 residues on the 190's loop" *J. Biol. Chem.* (Feb. 1997) 272(8):5076–5081, http://www.medscape.com/server-jav...d96–97+247339+(giroux:au+and+loop), One page total.

Internet abstract of Maekawa et al., "Detection and characterization of new genetic mutations in individuals heterozygous for lactate dehydrogenase–B(H) deficiency using DNA conformation polymorphism analysis and silver staining" *Hum. Genet.* (Mar. 1993) 91(2):163–168, http://www.medscape.com/server-jav...(maekawa:au+and+'silver+staining'), One page total.

Internet abstract of Mainhart et al., "A three–dimensional model of an anti–lysozyme antibody" *J. Mol. Biol.* (1987) 194:713–724, http://ncbi.nlm.nih.gov/htbin–...uery?uid+196584&form=6&db=n&Dopt=g/ (One page total).

Internet Abstract of Miyazaki et al., "Chemical modification and site–directed mutagenesis of Tyr36 of 3–isopropyl-malate dehydrogenase from Thermus thermophilus HB8" *Protein Eng.* (Jan. 1994) 7(1):99–102, http://www.medscape.com/server-jav...(oshima:au+and+'thermophilus+HB8'), One page total.

Internet Abstract of Truong et al., "Inactive and temperature–sensitive folding mutants generated by trptophan substitutions in the membrane–bound d–lactate dehydrogenase of *Escherichia coli*" *Biochemistry* (Nov. 1991) 30(44):10722–10729, http://www.medscape.com/server-jav...508057+(truong:au+and +'d–lactate), One page total.

Internet abstract of Wagner et al., "Site directed mutagenesis: a tool for enzyme mechanism dissection" *Trends Biotechnol.* (Sep. 1990) 8(9):263–270, http://www.medscape.com/server-jav...63583+(benkovic:au+and+dissection), One page total.

Internet abstract of Wigley et al., "Structure of a ternary complex of an allosteric lactate dehydrogenase from *Bacillus stearothermophilus* at 2.5 A resolution" *J. Mol. Biol.* (Jan. 1992) 223(1):317–325, http://www.medscape.com/server–jav...6087+(wigley:au+and+dehydrogenase), One page total.

Joh et al., "Cloning and sequence analysis of cDNAs encoding mammalian mitochondrial malate dehydrogenase" *Biochemistry* (1987) 26:2515–2520.

Klein et al., "Equilibrium and kinetic aspects of the interaction of isolated variable and constant domains of light chain with the Fd fragment of immunoglobulin G" *Biochemistry* (1979) 18:1473–1481.

Lavoie et al., "Experimental analysis by site–directed mutagenesis of somatic mutation effects on affinity and fine specificity in antibodies specific for lysozyme" *J. Immunol.* (1992) 148:503–513.

Maenaka et al., "A stable phage–display system using a phagemid vector: phage display of hen egg–white lysozyme (HEL), *Escherichia coli* alkaline, phosphatase, and anti––HEL monoclonal antibody, HyHEL–10" *Biochem. Biophys. Res. Comm.* (1996) 218:682–687.

Mallender et al., "Comparative properties of the single chain antibody and Fv derivatives of mAB 4–4–20. Relationship between interdomain interactions and the high affinity for fluorescein ligand" *J. Biol. Chem.* (1996) 271(10):5338–5346.

McCafferty, J. et al., "Phage antibodies filamentous phage displaying antibody variable domains" *Nature* (1990) 348(6301):552–554.

Mei et al., "Vasoactive intestinal peptide hydrolysis by antibody light chains" *J. Biol. Chem.* (1991) 266:15571–15574.

Muyldermans et al., "Sequence and structure of VH domain from naturally occuring camel heavy chain immunoglobulins lacking light chains" *Protein Engineering* (1994) 7:1129–1135.

Padlan et al., "Structure of an antibody–antigen complex: crystal structure of the HyHEL–10 Fab–lysozyme complex" *Proc. Natl. Acad. Sci. USA* (1989) 86:5938–5942.

Parsons et al., "Directing phage selections towards specific epitopes" *Protein Engineering* (1996) 9(11):1043–1049.

Riechmann et al., "Expression of an antibody Fv fragment in myeloma cells" *J. Mol. Biol.* (1988) 203:825–828.

Smith–Gill et al., "A three–dimensional model of an anti–lysozyme antibody" *J. Mol. Biol.* (1987) 194:713–724.

Smith–Gill et al., "Contributions of immunoglobulin heavy and light chains to antibody specificity for lysozyme and two haptens" *J. Immunol.* (1987) 139:4135–4144.

Sun et al., "Antigen recognition by an antibody light chain" *J. Biol. Chem.* (1994) 269:734–738.

Tang et al., "A high affinity digoxin–binding protein displayed on M13 is functionally identical to the native protein" *J. Biol. Chem.* (1995) 270(14):7829–7835.

Tsumoto et al., "Contribution to antibody–antigen interaction of structurally perturbed antigenic residues upon antibody binding" *J. Biol. Chem.* (1994) 269:28777–28782.

Tsumoto et al., "Effect of the order of antibody variable regions on the expression of the single–chain HYHEL10 FV fragment in *E. coli* and the thermodynamic analysis of its antigen–binding properties" *Biochem. Biophys. Res. Comm.* (1994) 201:546–551.

Tsumoto et al., "Role of Tyr residues in the contact region of anti–lysozyme monoclonal antibody HyHEL–10 for antigen binding" *J. Biol. Chem.* (1995) 270:18551–18557.

Tyutyulkova et al., "Selection of functional human immunoglobulin light chains from a phage–display library" *Appl. Biochem. Biotechnol.* (1994) 47:191–198.

Ueda et al., "Analysis of intramolecular interaction of an antibody Fv region and its application to immunoassay" Abstracts of the 8th Annual Meeting of the Protein Engineering Society of Japan, *Protein Engineering* (1996) 9(9):819 (Abstract 21).

Ueda et al., "Antigen responsive antibody–receptor kinase chimera" *Bio/Technology* (1992) 10:430–433.

Ueda et al., "Open sandwich ELISA: a novel immunoassay based on the interchain interaction of antibody variable region" *Nature Biotechnology* (1996) 14:1714–1718.

Ueda et al., "Synthesis and expression of a DNA encoding the Fv domain of an anti–lysozyme monoclonal antibody, HyHEL10, in *Streptomyces lividans*" *Gene* (1993) 129:129–134.

Ward et al., "Binding activities of a repertoire of single immunoglobulin variable domains secreted from *Escherichia coli*" *Nature* (1989) 341:544–546.

Schmidt et al., Prot. Engineering 6(1):109–122.

Polymenis et al., J. Immunol. 154:2198–2208.

William Huse "Combinatorial Antibody Expression Libraries in Filamentous Phage", In: Antibody Engineering, A Practical Guide, 103–120.

Pluckthun A., "Mono– and bivalent antibody fragments produced in *Escherichia coli:* Engineering, Folding, and Antigen Binding", In: Immunol. Rev. (Denmark) 130:151–88, Dec. 1992.

\* cited by examiner

SEQUENCE LISTING

```
<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 1
tttggcccag ccggccatgg cc                                               22

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 2
tttgcggccg ccgccgagac ggtgacgagg gt                                    32

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 3
ccgcggccgc gggtacccca gaaatgcctg ttctagaaa                             39

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 4
aagcggccgc cttaagcccc agagcggc                                         28

<210> SEQ ID NO 5
<211> LENGTH: 17
<212> TYPE: DNA
<213> ORGANISM: Artificial Sequence
<220> FEATURE:
```

-continued

```
<223> OTHER INFORMATION: Description of Artificial Sequence:SYNTHETIC
      DNA

<400> SEQUENCE: 5
ttaatacgac tcactat                                                        17

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence:SYNTHETIC
      DNA

<400> SEQUENCE: 6
tttaagcttg gactcacccg ccgagacggt gacgac                                   36
```

METHOD FOR MEASURING ANTIGEN CONCENTRATION

This application is a continuation application of Ser. No. 08/663,922 filed Jun. 14, 1996, now U.S. Pat. No. 5,981,199.

BACKGROUND OF THE INVENTION

The present invention relates to a method for measuring antigen concentration in a sample. It relates more specifically to a new method for making more simple and highly sensitive measurements of antigen concentration by employing intramolecular interactions between components of antibody (immunoglobulin). This method can be utilized as, for example, a sandwich ELISA method, and is useful for clinical diagnosis of the concentrations of various antigens in biological samples (blood, urine and body fluid). It is also applicable to the specific detection of all other sorts of substances, both natural and unnatural, recognizable as an antigen, and can be used as research and industrial sensors.

DESCRIPTION OF RELATED ART

Conventionally, various methods for measuring antigen concentration have been known, some of which are used for clinical diagnosis. Of these methods for measuring antigen concentration, the one commonly called sandwich ELISA method (or sandwich PTA method) attracts special attention. This method is characterized by measuring the concentration of antigen using two kinds of monoclonal antibodies which recognize different epitopes of the antigen, alternately, with one kind of monoclonal antibody and one kind of polyclonal antibody. The procedure of this sandwich ELISA consists of three stages. In the first stage, an antigen-containing sample is poured on a measurement plate on which monoclonal/polyclonal antibodies (primary antibodies) have been adsorbed; the antigens in sample are bound to the primary antibodies. In the second stage, the substances in the sample other than the antigen are washed off with a washing agent. Then, in the third stage, a solution of the secondary antibodies, labeled with reporter molecules, such as an enzyme or radioisotope, are poured on the plate; the labeled antibodies bind to the antigens having been bound to the primary antibodies.

Excessive labeled antibodies are fully rinsed away with washing agent, then the amount of the reporter molecules left in the measurement plat 0 is measured by means of an enzyme activity reader or a liquid scintillation counter; and the observed values are used for the estimation of the quantity of antigens in the sample.

The conventional sandwich ELISA method consists of the operation steps as described above, and it has the advantage of being capable of measuring essentially all kinds of protein antigens, so long as the necessary antibodies are available. On the other tend, however, the measurement procedure Involves at least two cycles of reaction and washing, and inevitably becomes complicated, time-consuming and costly when it is to be automated.

SUMMARY OF THE INVENTION

In order to solve the aforestated problems associated with the conventional ELISA method, the present invention provides a new method which permits simpler and speedier measurements of antigen concentration.

The first method according to the instant invention is a method for measuring an antigen concentration in a sample, which comprises:

(a) preparing VH-domain polypeptide and VL-domain polypeptide of an antibody specific to the antigen;

(b) labeling one of the polypeptides with a reporter molecule to form labeled polypeptide, and immobilizing the other polypeptide onto a solid-phase to form immobilized polypeptide;

(c) contacting the antigen-containing sample and the labeled polypeptide with the solid-phase; and, (d) measuring the reporter molecule of the labeled polypeptide bound to the immobilized polypeptide.

One embodiment of the first method in this invention is that the polypeptide to be immobilized onto solid-phase is preferably biotinylated or modified with a tag sequence, and the solid-phase adsorbs or chemically bonds avidin or streptavidin, thereby immobilizing the polypeptide onto the solid-phase through biotin-avidin binding or tag sequence-streptavidin binding.

Another embodiment of the first method is that the reporter molecule is filamentous phage which is fused to the polypeptide, in which case the filamentous phage is preferably labeled with an enzyme or a fluorochrome.

A further embodiment of the first method is that the reporter molecule is an enzyme, in which case the enzyme is preferably alkaline phosphatase originated from *Escherichia coli*.

A further embodiment of the first method is that the reporter molecule is a fluorochrome, in which case the fluorochrome is fluorescein or a derivative thereof.

The second method according to the present invention is a method for measuring an antigen concentration in a sample, which comprises:

(a) preparing VH-domain polypeptide and VL-domain polypeptide of an antibody specific to the antigen;

(b) labeling tho VH-domain polypeptide with a 1st reporter molecule, and labeling the VL-domain polypeptide with a 2nd reporter molecule;

(c) mixing the labeled VH-domain polypeptide and the labeled VL-domain polypeptide with the antigen-containing sample; and (d) measuring a changed characteristic value of the 1st reporter molecule or the 2nd reporter molecule which is induced by the interaction of both molecules.

One embodiment of the second method in this invention is that the 1st reporter molecule and the 2nd reporter molecule are fluorochromes of different kinds, and change of fluorescence intensity induced by energy transfer between both fluorochromes is used to measure the amount of the VH-VL complex. In this case, the fluorochromes are preferably fluorescein or a derivative thereof and Rhodamine or a derivative thereof.

Having the aforestated constituents, the first and the second methods according to the present invention describe a new ELISA process which permits simpler and quicker measurements of antigen concentration while offering the same or higher level of sensitivity and reliability as compared with the sandwich ELISA method conventionally available. The present invention was based on the phenomenon, as previously unnoticed, that the stability of the variable Fv-domain regions (VH-domain region and VL-domain region) of an antibody varies significantly depending upon the presence or absence of an antigen to be bound to the Fv-domain, and this invention makes active use of this property to conduct measurements of the concentration of antigen.

In addition, the present invention also provides a labeled polypeptide, a set of labeled polypeptides and a kit for measuring an antigen concentration in a sample.

Then, the present invention will be described in detail, in which VH-domain polypeptide may be referred to as VH, and VL-domain polypeptide as VL.

DETAILED DESCRIPTION OF INVENTION

Figure 1:
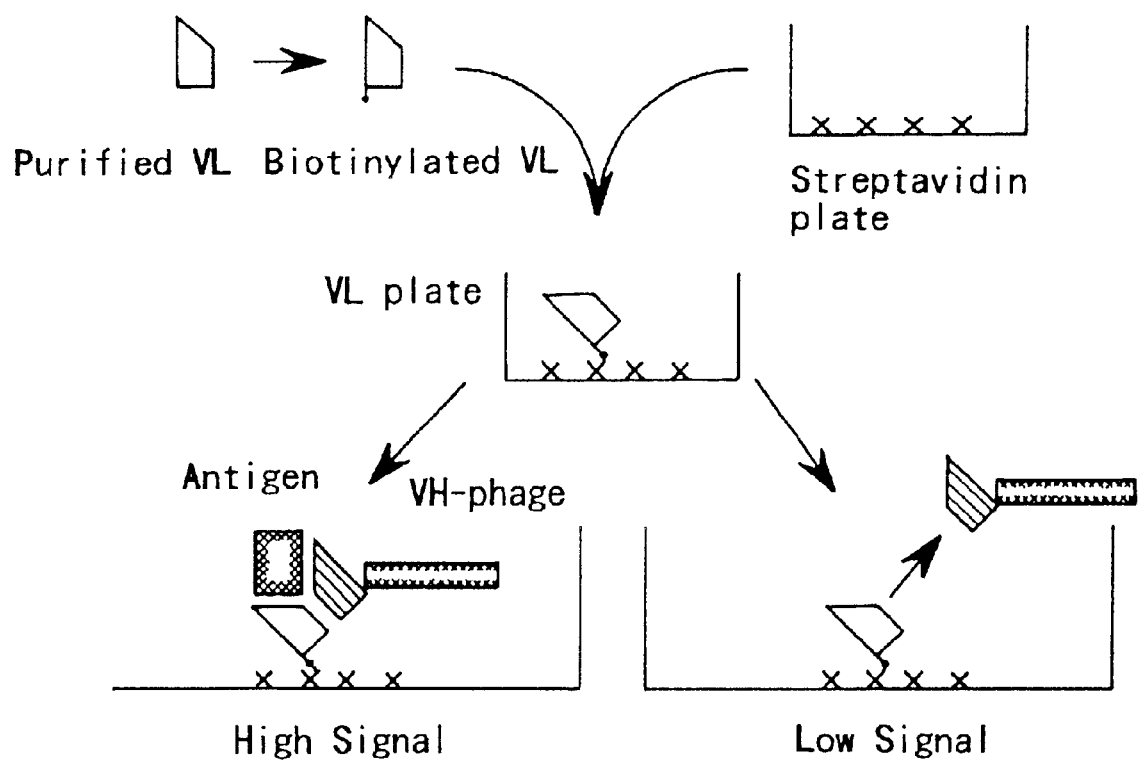
FIG. 1 is a block diagram illustrating the procedure for measuring an antigen concentration in a sample according to the present invention.

The method of this invention uses an antibody that can specifically bind a desired antigen, and such antibody can be obtained from monoclonal antibodies prepared by the hybridoma technology, for example Then, from such antibody, VH-domain and VL-domain polypeptides are prepared respectively. The polypeptides can be more or less of VH and VL domains of antibody, so long that a paired form of the polypeptides will specifically bind the desired antigen. The preparation of these polypeptides is accomplished by, for instance, making of a monoclonal antibody which specifically binds a desired antigen by known methods (Kohler, G. and Milstein, C., Nature 256, 495–496, 1975), and obtaining the CDNA which encodes the antibody variable regions by either the method using CDNA library and hybridization (Sambrook, Fritsch, and Maniatis, Molecular Cloning 2nd ed., 1989) or the method using PCR (Larrick et al., Biochem. Biophys. Res. Commun. 160, 1250–1256, 1989; Jones, S. and Bendig. M., Bio/Technology 9, 88–89, 1991) enable us to clone the antibody genes into a vector plasmid. After subcloning the gene for VH and/or VL region to an appropriate expression vector and expressing the gene in host cells, necessary amounts of VH and/or VL of the antibody recognizing the specific antigen can be obtained. To obtain VH and/or VL coding genes from antibody cDNA, either method of digesting the desirable sequence region by appropriate restriction enzyme and amplifying it with cloning vector, or amplifying the desirable sequence by PCR, can be employed. In the case of the VH and/or-VL being expressed in host cells, any gene coding appropriate reporter protein can be cloned into the expression vector, so that the VH and/or VL can be expressed as fusion or chimeric protein with the reporter protein. Alternatively, the VH and/or VL also can be obtained by proteolytic digestion of a desired antibody-protein and subsequent purification. In this case, the polypeptides can be obtained without the step of cDNA cloning, though careful purification and labeling reaction of the polypeptides are required.

By the first method of this invention, one of these polypeptides is immobilized onto the solid-phase to form an immobilized polypeptide and the other is labeled with a reporter molecule to form a labeled polypeptide. Both VH and VL can be useful as immobilized and/or labeled polypeptides. Any conventional method can be used to immobilize the polypeptides to the plate. Also, any conventional reporter molecule or label can be used in this invention, and the reporter molecule or label can be labeled on the polypeptides by the known methods. Examples of the reporter molecule include a filamentous phage. When VH, for example, is labeled with this filamentous phage, the VH gene is integrated into a vector plasmid so that the VH can be expressed as a fusion protein with the coat protein g3p of the filamentous phage. Thereafter, the VH-g3p fusion protein expressed is displayed on M13 phages (VH-phages). This is made possible by use of the known technology called phage display (McCafferty, J. et al. Nature 348. 55–554, 1990). This method consists of infecting the M13phages with $E.\ coli$ having a fusion protein-expression vector plasmid and of cultivating the transformant cells under conditions which induce the expression of the fusion protein. This process can give said phage in the supernatant of the culture broth. The VL fragment can also be expressed in the form of fusion protein with a proper secretion signal, and can be produced also using $E.\ coli$. In this invention, however, the methods for preparing these VH and VL are not restricted to those referred to above. Any know method that produces the same result can be employed.

Now, referring to FIG. 1, an example of the operation procedures according to the first method of this invention will be described. In this figure, VH is the phage-labeled polypeptide and VL is the immobilized polypeptide.

First, VLs are immobilized on a measurement plate. For this purpose, it is preferable to previously purify and biotinylate the VLs. The biotinylated VLs can be efficiently immobilized with avidin or streptavidin adsorbed on a measurement plate. Alternately, VLs can be modified with an amino acid sequence at the carboxyl terminal, which sequence is capable of binding to streptavidin This method requires no special purification process; all that is needed is an incubation of the supernatant of the culture broth with a streptavidin plate.

The method according to the instant invention theoretically requires only one cycle of reaction and washing for the whole process of measurement. More specifically, the method consists of simultaneously introducing a sample containing the target antigen and VH-phages into a plate on which VLs are immobilized on their solid-phase. The sample and VH-phages are mixed in the plate, then they are preserved on the plate for a duration. In the absence of an antigen, VH-VL interactions are so weak that no binding of the phages to the plate can occur. In the presence of an antigen, on the other hand, VHs and VLs bind strongly to each other together with the antigen, and this causes the phages to be immobilized on the solid-phase. The measurements of the phages left on the washed plate are correlated highly significantly with the concentration of the antigen In the sample. quantitative determination of the phages can be accomplished conveniently by the ELISA, using a commercially available peroxidase labeled anti-M13 phage antibody. In order to take advantage of the method of this invention, however, it is desirable to previously label the phages either with a fluorochrome or with an enzyme, permitting the succeeding measurement process to be initiated immediately after washing. Heretofore, if the VH-domain fragment alone of a certain kind of antibodies is employed for the measurement of antigen, the stability of reagents could sometimes call into question due to the highly hydrophobic property thereof.

Use of the phage technology eliminates such stability problem for at least three months as long as the phage solution is sterilized through filter and kept at 4° C.

Another embodiment of the first method of the invention is that an enzyme or a fluorochrome may be employed as a reporter molecule. When an enzyme (e.g. alkaline phosphatase) Is employed for labeling, VH or VL gene is inserted into a vector so that the VH or VL is expressed as fusion protein with the enzyme, and labeled polypeptide is prepared as such. When a fluorochrome (e.g., fluorescein or its derivative) Is employed, the amino terminal of VH or VL gene is selectively labeled with the fluorochrome, and this permits the preparation of labeled polypeptide without affecting the ability thereof to bind to antigen or to form Fv complex. When these reporter molecules are used, an antigen concentration can be measured by the same procedures as indicated in FIG. 1, whereby an antigen-containing sample and labeled polypeptide are poured in a plate and washed, followed by the detection of the enzyme activity or the amount of dye by the known method.

The first method of this invention can do with a combination of immobilized and labeled polypeptides previously prepared from an antibody against the subjected antigen. Also, such combination of the polypeptides can be constructed as a kit which comprises a solid-phase having an immobilized VL or VH and a reagent containing a labeled VH or VL. The solid-phase can be prepared by immobilizing VL or VH with the above described or any known methods, and the labeled VH or VL can be prepared by labeling it with any one of the forementioned reporter molecules or others. In this kit of this invention, it may be useful to add a standerd solution of the subjected antigen for preparing a standerd curve in order to measure the unknown antigen concentration in a sample.

Moreover, in the case of the repoter molecule being enzyme, a subtrate for the enzyme should be required as a component of the kit A specific washing agent for rinsing away excessive labeled polypeptides may be a component of the kit.

Next, the second method for measuring an antigen concentration according to the present invention will be described. This method consists of mixing the VH-domain polypeptide labeled with the 1st reporter molecule and the VL-domain polypeptide labeled with the 2nd reporter molecule together with an antigen-containing sample, then using a changed characteristic value of the 1st reporter molecule or the 2nd reporter molecule which is induced by the interaction of both molecules as indicator for the measurement of the amount of Fv formed by both polypeptides. This eliminates the need for the preparation of immobilized polypeptide onto the solid-phase, and also does away with the step of washing the excessive labeled polypeptide left thereafter.

The 1st reporter molecule and the 2nd reporter molecule may be fluorochromes of different kinds having different fluorescent wavelengths and excitation wavelengths (e.g., fluorescein and Rhodamine X). If these fluorochromes approach each other closer than the specified distance (approximately 4 nm), a phenomenon referred to as "fluorescence resonance energy transfer" occurs between the fluorochromes, and causes one fluorochome to be used for the excitation of the other, bringing about a fluorescence of longer wavelengths. More specifically, fluorescein is excited at 490 nm and emits a fluorescence of 530 nm, but in the presence of Rhodamine X in the vicinity thereof, the fluorescent energy near 530 nm transfers to the Rhodamine X, causing a fluorescence of longer wave length (603 nm) to be emitted. The distance, known up to the present through X-ray structural analyses, between the amino terminals of the VL and VH chains of an antibody molecule is approximately 3.5 nm, a distance enough to detect a fluorescence resonance energy transfer.

Accordingly, by labeling the amino terminals of VH and VL with different kinds of fluorochromes and using a changed value of fluorescent intensity ratio between two fluorochromes as indicator, it is possible to measure the amount of the VH-VL complexes. As discussed above, the amount of the VH-VL complexes depends on an antigen concentration, and accordingly, the detection of that value ensures the accurate measurement of the antigen concentration.

The second method of this invention can do with a set of the VH labeled with the 1st reporter molecule and the VL with the 2nd reporter molecule, and the set of the polypeptides can be constructed as a kit which comprises a 1st reagent containing the labeled VH and a 2nd reagent containing the labeled VL. In this kit, it may be useful to add a standard solution of the subjected antigen for preparing a standard curve.

The present invention will be described in more detail with the following Examples.

EXAMPLE 1

With filamentous phage as a reporter molecule, the concentration of hen egg lysozyme (HEL) was measured.

(a) Preparation of VL-Domain Polypeptide of HyHEL-10:

From the vector plasmid pKTN2 (Tsumoto, K. et al., J. Biol. Chem. 69, 28777–28782, 1994) which encodes pelB signal peptide sequence upstream of the structural genes of VH and VL of the antibody HyHEL-10 which is specific to HEL, the 670bp portion thereof encoding the pelB, VL And ssl transcription termination sequence are cleaved by the restriction enzymes, NheI and EcoRI, and purified in agarose electrophoresis. This DNA fragment was ligated with the DNA fragment obtained by digesting the vector pET20b having a T7 promoter (Novagen Inc.) by using the restriction enzymes XbaI and EcoRI, to prepare VL-expression vector pETVLhel. Then, *E. coli* BL21(DE3) having T7 polynerase gene on its genome was transformed with this vector, and the transformant cells were cultivated at 30° C. in LB medium. When the cells reached-a saturation density in 1 liter medium, they were collected with centrifugation, and re-suspended in 1 liter of fresh LB medium containing 0.5 m MPTG and then cultured continuously for further 24 hours. The cells were again collected with centrifugation, and then ammonium sulfate was added to the supernatant thereof until 66% saturation, thereby precipitating the protein in the supernatant. The precipitates were collected by centrifugation and dissolved in a small amount of water. The aqueous solution was dialyzed into 10 mM phosphate buffer (pH7.0), and subsequently, ¼ volume of DEAE cellulose was added to adsorb the protein other than VL in the medium. Repeating this process two more times could give VL-domain polypeptide with a purity of 95% or higher.

(b) Preparation of The VH-Domain Polypeptide of HyHEL-10, Displayed on M13 Phage:

Firstly, a vector plasmid pluck2001 was prepared by altering the vector portion pTZ18U of pluck2000 (Japanese Patent Publication No. 129516/1995) to pTZ19U. This pluck2001 possesses pelB signal peptide sequence, the part of VL and VH structural genes of HyHEL-10, c-myc tag, C-terminal of M13 phage gent 3 protein (g3p), M13 origin, ampicillin resistance gene, and an origin derived from plasmid pUC series. The following operations were performed to remove the VL structural gene from the vector plasmid pluck2001. That is, in order to combine the pelB signal sequence and VH structural gene with the downstream c-myc tag and g3c C-terminus in matching reading frame of their codon, PCR reaction was conducted by using 1 ng of pluck2001 as template and 50pmol each of primers identified in SEQ ID NOs.1 and 2, respectively, in a 100 µl of reaction liquid containing 2.5-unit Pfu DNA polymerase (Stratagene), dNTPs with final concentration of 0.2 mM and 10 µl of 10×reaction liquid. The thus obtained 380bp DNA fragments were then digested with the restriction enzymes SfiI and NotI, and were ligated with 1 fragments of pluck2001 vector having been digested with SfiI and NotI. From the restriction enzyme analyses of the resultant plasmid, it was confirmed as the target one and was named pluck2010. E. coli XL-1Blue (Δ(lac), end A1, gyrA96, hsdR17(rk⁻, mk⁺), recA1, relA1, supE44, thi1, [F', lacIq, lacZ α M15, proAB, Tm10(tet')))  was transformed with the pluck2010, and the colony was cultivated overnight at 37° C. in 5 ml of LB medium containing 12.5 mg/l of tetracyclin and 1% glucose. From this culture, 50 µl was taken out and mixed with 25 µl of ML13VCS phage (Stratagene SC200251, >10$^{11}$ pfu/ml), at 37° C. for 20 minutes. Then, the mixture was transferred into a 5 ml of LB medium containing 100 mg/l of ampicillin and 70 mg/l of kanamycin, and was cultured with various shaking at 37° C. for 16 hours. The culture was centrifuged to remove the cells, and the supernatant thereof was preserved at 4° C. till it was used as a phage solution.

(c) Immobilizing of VL and HEL to a Microtiter Plate, and ELISA using the VH-Phage:

In order to immobilize VLs and HEL to a microtiter plate, they were biotinylated with biotin NHS (Pierce) according to the product manual. A PBS (10 mM phosphate buffer:pH7.2, 150 mM NaCL) solution containing 10 µg/ml of streptavidin (Wako) was poured into a microtiter plate (Falcon 3912) at a rate of 100 µl per well and preserved at 4° C. overnight to adsorb the streptavidin to the plate After the solution was removed, the plate was blocked with 200 µl of binding buffer (2% skimmed milk/PBS) for one hour at room temperature. The streptavidin plate thus obtained was washed twice with PBS containing 0.1% Tween 20 (PBS-T), and in succession, the biotinylated lysozyme which was diluted with PBS so that the concentration thereof was 10 µg/l, was poured by 100 µl into the plate and preserved at room temperature for one hour. After removing the solution, the plate was rinsed trio times using PBS-T. Into this plate were added 10 µl of sample in which 0, 0.1 µg/ml or 10 mg/l of VLs were contained in PBS, and 90 µl of VH-phage solution which had been mixed with the equivalent amount of binding buffer 30 minutes before, and the resulting mixture was incubated at 37° C. for one hour. After further two times of washing, 100 µl of 1/5000 diluted peroxidase-labeled anti-M13 antibody (Pharmacia) in binding buffer was added. The plate was washed five times after one hour at 37° C., and then the sample was measured for absorbance at 490 nm by the ordinary color development method using orthopenyl enediamine for the quantitative determination of the M13 phage fixed on the plate.

Another cycle of experiment was also conducted using biotinylated VLs instead of biotinylated lysozyme and lysozyme instead of the VLs as a sample, and the result obtained were compared with that of the first experiment.

Figure 2:
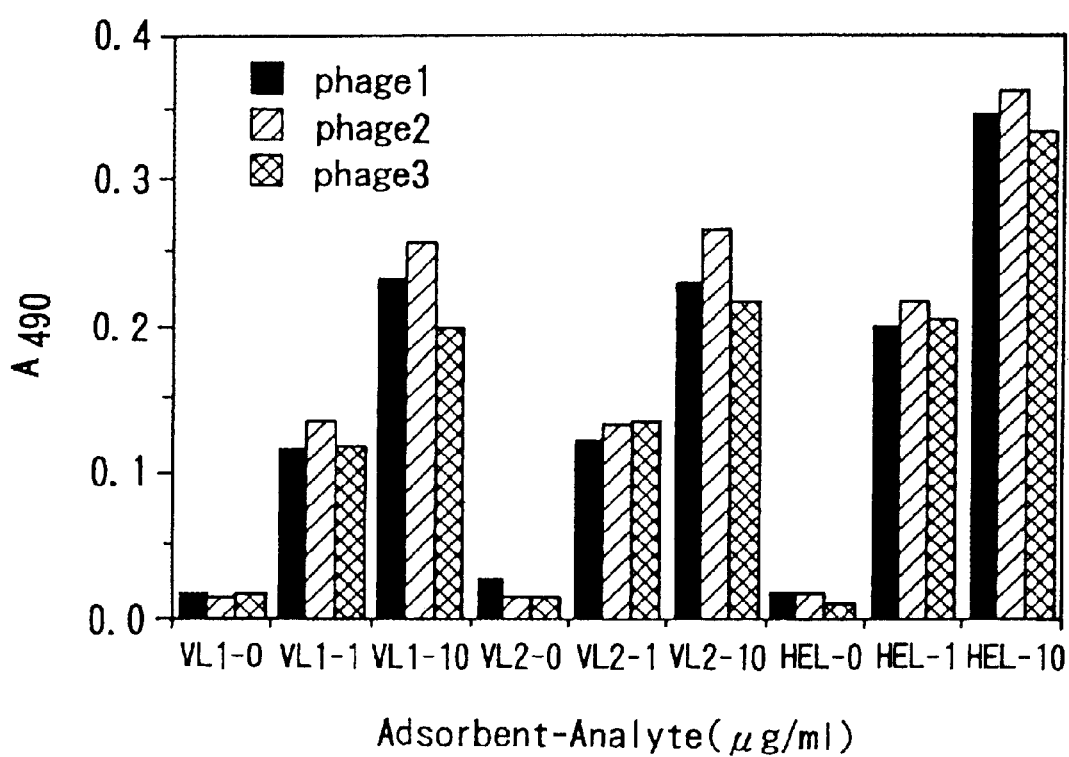
FIG. 2 is a bar graph indicating the amount of VH phage bound to the biotinylated VL or biotinylated hen egg lisozyme (HEL), in the presence of variable analysis.

The results are indicated in FIG. 2. In the figure, VL1-0 means that the batch 1 of biotinylated VLs was immobilized onto solid-phase in a plate, and VH-phages and 0 µg/ml of HEL were added thereto for incubation. In this case, the batch 1 of biotinylated VLs was prepared by mixing 500 µg of purified VL in 350 µl of 0.1 mol/l NaHCO$_3$:pH8.3, 150 mmol/l NaCl and 100 µg of biotin-NHS in 3.5 µl of DMSO were mixed, reacting at room temperature for 30 minutes, and thereafter, dialyzing into PBS containing 0.02% sodium azide For the VL1, measurement were made with samples having HEL concentrations of final 0.1 and 10 µg g9ml, respectively. When the batch 2 of biotinylated VL, i.e., VL2 (prepared using 1 µl of biotin-NHS solution instead of 3.5 µl of biotin-NHS solutions of VL1) was immobilized onto solid-phase, measurements were also conducted in a similar way. Furthermore, HEL-0 means that biotinylated HEL was immobilized onto solid-phase in a plate, VLs with a concentration of 0 µg/ml, together with VH-phages, was added thereto for incubation. Tested concentrations of VLs were 0 µg/ml, 1 µg/ml and 10 µg/ml. The VH-phages were prepared from three kinds of phage samples of independent colonies (phage 1, 2 and 3).

As is shown in FIG. 2, it was confirmed that the amount of bounded M13 phages increased with increasing concentrations of the co-existing protein (HEL or VL) in a sample, in both cases where VLs and HEL were immobilized onto solid-phase in a plate.

(d) Measurement of the HEL Concentrations in a Sample by ELISA using VH-Phages:

Similarly as in the procedures (c) above, by immobilizing biotinylated VLs on solid-phase in a plate, and by varying HEL concentrations in a sample, the amount of bounded VH-phages were measured, and a calibration curve was drawn based on the measurements.

Figure 3:
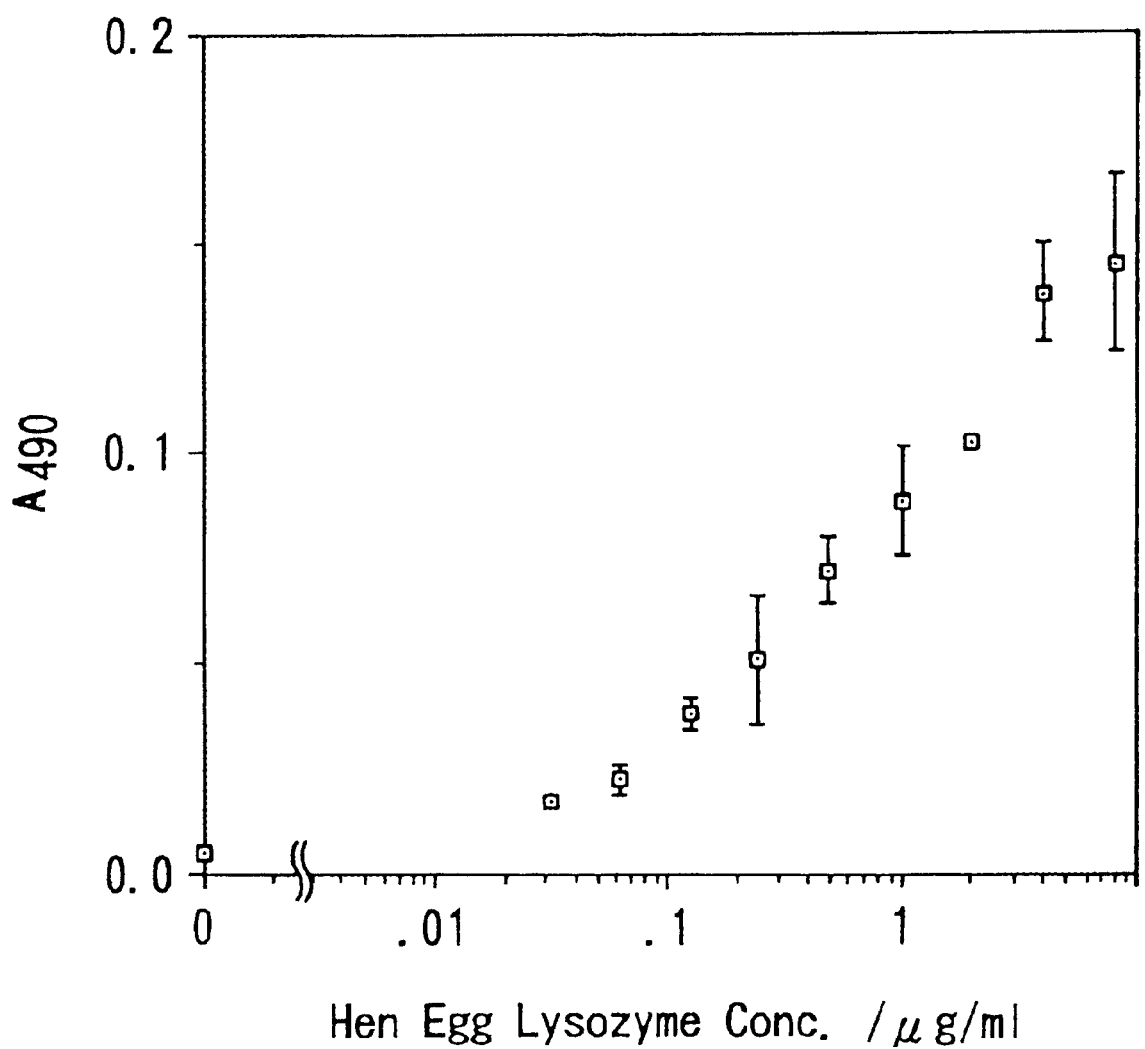
FIG. 3 is a calibration curve for the concentration of HEL prepared on the basis of the amount of VH phage bound to the biotinylated VL which is immobilized on solid-phase in a plate.

The results are shown in FIG. 3, which indicates that the method of the instant invention is highly sensitive and reproducible enough to measure antigen of which final concentration is 0.015 µg (15 ng)/ml or higher. This sensitivity is essentially the same as the one provided by the conventional sandwich ELISA method.

EXAMPLE 2

Using alkaline phosphatase as a reporter molecule, HEL concentrations in a sample were measured.

(a) Preparation of the Expression Plasmid for E. coli Alkaline Phosphatase:

The chromosome DNA of E. coli XL1-blue was extracted by the known method (Sambrook, Fritsh, Maniatis, "Molecular Cloning, Ver 2", 1989), and the 1450bp portion encoding alkaline phosphatase (the gene: PhoA, EC3.1.3.1) was amplified by PAR. To add to the terminals of the PCR products the NotI site, the oligonucleotides of SEQ ID NOs. 3 and 4 were used as PCR primers. More specifically, 35 cycles of PCR processes were conducted with 1 ng chromosome DNA of E. coli XL1-Blue as template DNA in a 100 µl of reaction liquid containing 50 pmol each of the primers, and 2.5 unit of Tag DNA polymerase (Perkin Elmers). The alkaline phophatase gene fragments obtained by the PCR were digested with the restriction enzyme NotI, and purified in agarose electrophoresis The expression vector pET20b (Novagen Inc.) was digested with NotI, treated with the phosphatase from bovine small intestine (Takara) and ligated with the alkaline phosphotase DNA fragment. From the restriction enzyme analyses of the resultant plasmid, it was confirmed as the target plasmid and was named pAP.

(b) Preparation of VH-Alkaline Phosphatase-Expression Plasmid:

From the vector plasmid pKTN2, the 480bp portion encoding pelB signal sequence and VH was amplified by PCR. To add 3'-terminal HindIII site to the PCR products, the oligonucleotides of SEQ ID NOs. 5 and 5 were used as PCR primers. More specifically, PCR reactions were conducted by using pKTN2 plasmid as template DNA in a 100 µl of reaction liquid containing the primers of each 50 pmol, and 2.5 unit Pfu DNA polymerase. The DNA fragments obtained were digested with EcoRV and HindIII, and purified by agarose electrophoresis. The resultant products were ligated with the pAP having been digested with EcoRV and HindIII, and purified by agarose electrophoresis, thereby preparing a VH-alkaline phosphatase (VH-AP)-expression plasmid. From the restriction analyses of the plasmid, it was confirmed as the target plasmid and was named as pVHAP.

(c) Expression and Purification of VH-AP Chimeric Protein in *E. coli.*:

The *E. coli* BL21(DE3)LysS having T7 polymerase on its genome was transformed with pVHAP by the calcium chloride method, and was cultivated at 37° C. overnight in an LB medium containing 1.5% agar and antibiotics (50 mg/l ampicillin and 34 mg/l chloramphenicol), to form colonies. These colonies were transferred to a 5 ml of LB medium containing antibiotics (50 mg/l ampicillin and 34 mg/l chloramphenicol), and were cultured at 28° C. overnight again. The cells reached to saturation density were collected by centrifugation, and were suspended in a 50 ml of fresh LB medium containing antibiotics (50 mg/l ampicillin and 34 mg/l chloramphenicol). Following this, they were cultured at 28° C. for three to four hours and were then transferred to one liter medium. When the cell density reached $OD_{6no}$=0.3–0.4, final 0.1 mM of IPTG was added to induce the expression of VH-AP chimeric proteins. The cells were cultured overnight, and using the 20 μl of culture liquid directly, they were subjected to SDS-polyacrylamide electrophoresis to confirm that the target proteins had been expressed. The cells were collected by centrifugation and dissolved in sonication buffer (59 mM $NaH_2PO_4$, 10 mM Tris-HCl:pH8.0). Then the cell wall was disrupted with a french press and the insoluble fractions were removed by ultracentrifugation using SW50.1 rotor (at 3200 rpm for one hour) to prepare lysate.

The obtained VH-AP chimeric protein was purified in two stages, one by TALON™ Metal Chelating Column, using 6×His sequence encoded at the C-terminus of the protein, and the second by the negative ion exchange column. First, the TALON™ metal chelating resin (by Clontech Laboratories Inc.; 2 ml for the column head) and 20 ml of protein solution were stirred gently in a 50 ml tube at 40° C. for one hour to adsorb the protein having a polyhistidine sequence onto the column. The resin was transferred to a 5 ml column, where it was washed and eluted with 20mM MES-Na buffer. Of the fractions obtained, those containing protein were collected and applied to a dialysis tube They were condensed by externally covering them with an adequate amount of PEG6000, then were dialyzed into 20 mM Tris-Cl solution (pH8.0) and applied to a negative ion exchange column (MonoQ HR5/5, Pharmacia) The resultant fractions were confirmed with the SDS polyacrylamide electrophoresis. Those containing the VH-AP chimeric proteins alone were collected and condensed, then dialyzed into Tris solution (0.1 M Tris-Cl, 0.1M NaCl: pH8.0). These successive purification operations proceeded up to a point where the target chimeric protein could be identified as a single band on SOS polyacrylamide electrophoresis. The proteins obtained were measured for concentration by means of BCA protein assay (Pierce), and preserved at 4° C. until they were used for measurement.

(d) Measurement of HEL Concentration Using VH-Alkaline Phosphatase:

Using a VL ,plate prepared similarly as in Example 1, 10 μl of sample containing various concentrations of HEL in PBS and 90 μg l of VH-AP Chimeric protein Solution (4 μg/ml in 0.1M Tris HCl: pH8.0) were added to their respective wells, and incubated at room temperature for two hours. Each well was washed four times using PBS containing 0.1% Tween (PBS-T), a substrate (1 mH 4-nitro phenylphosphate, Wako) was added at a rate of 100 μl per well, and 30 minutes and one hour thereafter, color development (yellow) was measured at absorbance of 410 nm.

Figure 4:
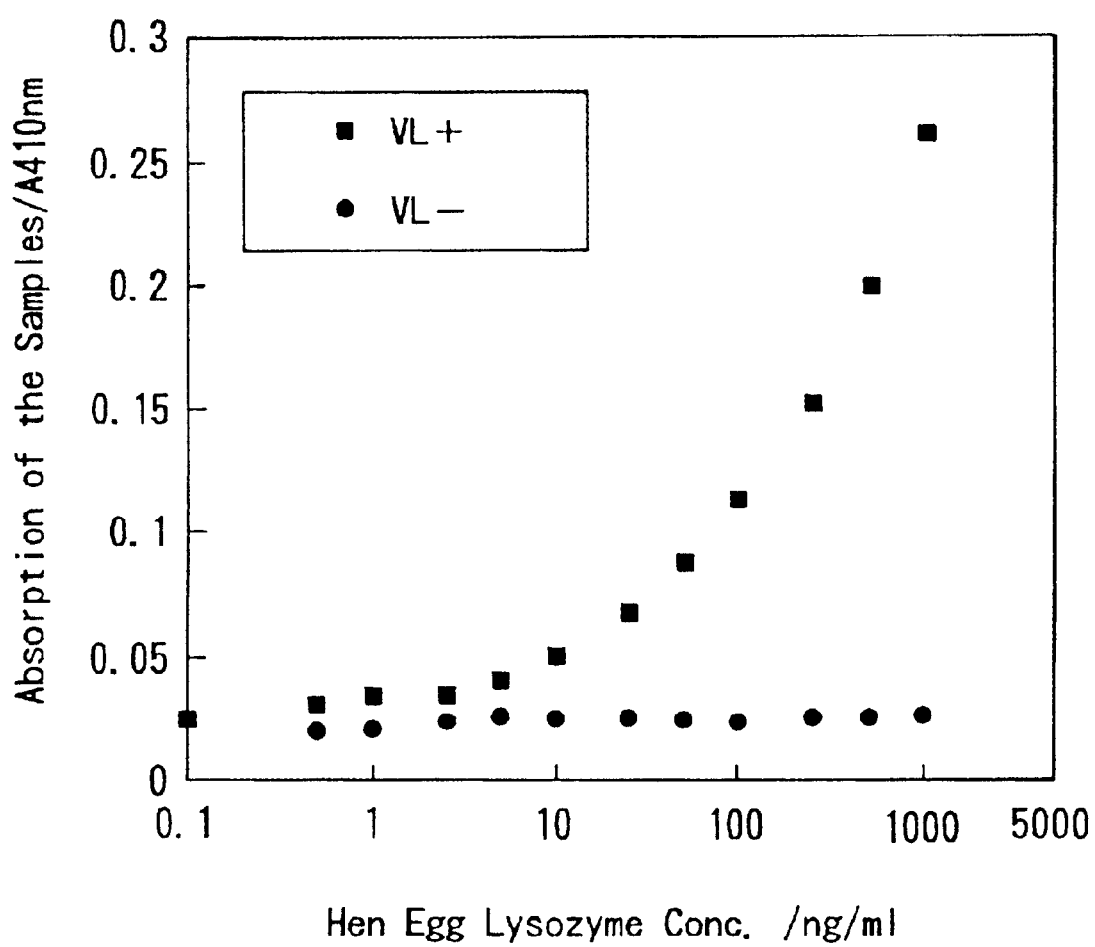
FIG. 4 is a graph plotting the HEL concentration vs. the absorption of samples which shows the amount of alkaline phosphatase-labeled VH bound to the biotinylated VL which is immobilized on solid-phase in a plate.

The results are shown in FIG. 4. This figure plots the absorbance against the final concentrations of HEL at one hour after the reaction, with the plotted figures being the means of the two measurements. As is evident from this figure, it was confirmed that the method of this invention assure highly sensitive and reproducible measurement of antigen substance with a final concentration of 1 ng/ml. The measurement sensitivity achieved by using this alkaline phosphatase as a reporter molecule is approximately tenfold of that recorded in Example 1. wherein filamentous phages were employed.

EXAMPLE 3

The association between fluorescein-labeled VH and Rhodamine X-labeled VL were detected in terms of fluorescence energy transfer.

(a) Preparation of VH and VL:

Using the structural genes of VH- and VL-domain of the antibody HyHEL-10 and the vector plasmid pKTN2, and also using the known procedure, Fv fragments of the HyHEL-10 were prepared. *E. coli* BL21 (DE3) was transformed with pKTN2, and cultured at 3020 C. in a 5 ml of LB medium containing 50 m/l ampicillin followed by successive culture in 50 m/l and one liter of medium, until the cell density reached saturation. After collecting the cells, they were cultured in the same medium containing 0.4 mM IPTG for 24 hours, and the supernatant from centrifugation was subjected to salting out using 66% saturated ammonium sulfate, and the precipitate was dialyzed into 50 mM phosphoric acid (pH7.2) and 0.2M NaCl. After one cycle of centrifugation (10 Krpm for 10 min.), the sample was adsorbed to the HEL affinity column equilibrated with-the same buffer (in which 10 mg/ml HEL is immobilized to CNBr activated Cepharose 4B made by Pharmacia Co. in accordance with the manual), washed with 100 ml of 0.1M Tris-HCl (pH8.5) and 0.5M NaCl, and eluted with 10 ml of 0.1M glycine buffer (pH2.0). Immediately after elution, the sample was neutralized with the equivalent amount of 1M Tris-HCl (pH7.5)

By this process, approximately 10 mg of Fv fragment was recovered. It was dialyzed into 50 mM Tris-HCI (pH8.8), and separated into VH and VL polypeptides in a negative ion exchange chromatography column (MonoQ HR5/5, Phamarcia Co.). Since few of the VL are adsorbed to the column, the VH and VL could be separated relatively easily, with the non-binding fractions taken as VL and the binding fractions as VH. The purity of both polypeptides after separation was found to be 90% or higher when confirmed by SDS polyacrylamide electrophoresis.

(b) Labeling of VH and VL with Fluorochrome:

285 μg of purified VH (0.5 ml) was dialyzed with 0.2M sodium pnosphate (pH7.0) and 0.1M NaCl 4.5 μl of 10 mM (about 5 mg/ml) fluorescein succinimide ester (Molecular Probes Inc., Eugene, USA) in dimethyl sulfoxide was added to this dialyzed substance. The mixture was stirred sufficiently and allowed to react at 4° C. for 10 hours. Concurrently, 4 μl of 10 mM (about 5 mg/ml) Rhodamine X succinimide ester (Molecular Probes Inc., Eugene, USA) in dimethyl sulfoxide was added to 235 μg of purified VL (0.5 ml) dialyzed into the same buffer. The mixture was stirred sufficiently and allowed to react at 4° C. for 10 hours. The molar ratio of protein to the dye was 1:2. The equivalent volume of 1M Tris-HCl (pH7.5) was added to terminate the reaction. The mixture was placed to gel filtration in PD-10 column (Pharmacia Co.) equilibrated with 0.2M sodium phosphate (pH7.0) and 0.1M NaCl to remove the dyes which had not been reacted.

(c) Measurement of HEL Concentrations:

20 μl of the fluorescein-labeled VH and 25 μl of the Rhodamine X-labeled VL were added to a solution composed of 0.2M sodium phosphate (pH7.0), 0.1M NaCl, and 1% bovine serum albumin. With the mixture placed Into a cuvette and by using HITACHI Type 850 Spectrofluorophotometer, emission spectrum was measured at 4° C. for the fluorescence wavelength ranging from 500 nm to 650 nm with 490 nm excitation. With continuous stirring, HEL was added to the mixture so that its final concentration was Increased successively from 10 ng/ml to 1 mg/ml, and the changes in emission spectra were recorded.

Figure 5:
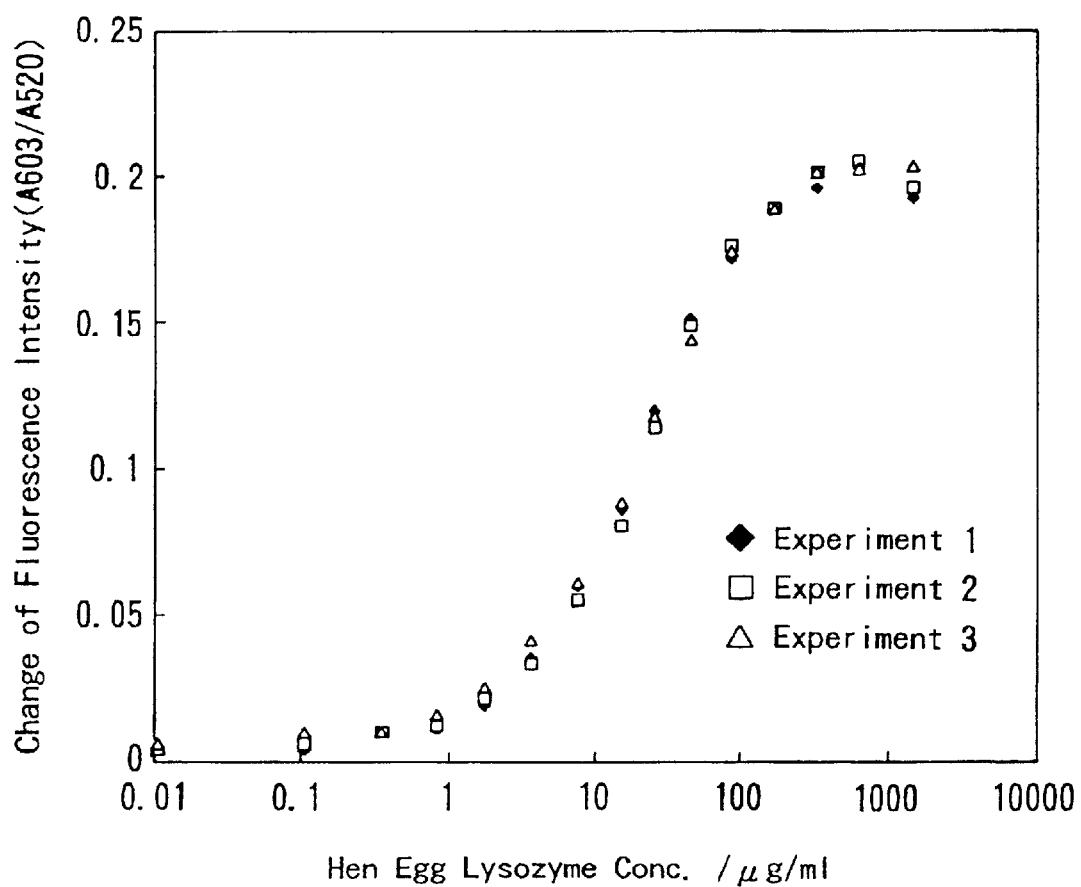
FIG. 5 is a graph plotting the HEL concentration vs. the increase In fluorescense intensity ratio between fluorescein-labeled VH and Rhodamine X-labeled VL.

As a result, it was observed that with increasing HEL concentrations, the fluorescence peak intensity at 530 nm decreased, and the energy transfer-derived fluorescence peak intensity at 603 nm increased. The time required for the change to occur was within a few seconds. Three independent experiments indicated that, as illustrated in FIG. 5, it became possible to measure antigen HEL concentrations reproducibly by taking the changed values in the ratio of fluorescence peak intensity between 620 nm and 530 nm.

What is claimed is:

1. A method of measuring the association of two polypeptides comprising:

obtaining a $V_H$-domain polypeptide having a first reporter molecule attached;

obtaining a $V_L$-domain polypeptide having a second reporter molecule attached;

mixing the two polypeptides with a compound that promotes association of the $V_H$- and $V_L$-domain polypeptides under conditions wherein the association of the $V_H$-domain polypeptide with the $V_L$-domain polypeptide is so weak in the absence of the compound that substantially no interaction between the first and second reporter molecules can occur without said compound; and measuring a characteristic value of the first reporter molecule or of the second reporter molecule which is induced by the interaction of the first and second reporter molecules upon association of the $V_H$-domain polypeptide with the $V_L$-domain polypeptide.

2. The method of claim 1 wherein one of either the $V_H$-domain polypeptide or the $V_L$-domain polypeptide is attached to a solid support.

3. The method of claim 1 wherein the first reporter molecule is a first fluorochrome and the second reporter molecule is a second fluorochrome.

4. The method of claim 1 wherein the first reporter molecule is fluorescein or a derivative thereof and the second reporter molecule is rhodamine or a derivative thereof.

5. The method of claim 1 wherein the first reporter molecule is rhodamine or a derivative thereof and the second reporter molecule is fluorescein or a derivative thereof.

6. An assay method for measuring the presence of, or quantifying the amount of, an analyte, comprising the steps of:

mixing a sample containing the analyte with a first modified polypeptide and a second modified polypeptide; said first modified polypeptide comprising a $V_H$-domain polypeptide having a first reporter molecule attached, and said second modified polypeptide comprising a $V_L$-domain polypeptide having a second reporter molecule attached wherein the association of the first modified polypeptide with the second modified polypeptide is so weak in the absence of the analyte that substantially no interaction between the first and second reporter molecules can occur without said analyte;

measuring a characteristic value of the first reporter molecule or of the second reporter molecule which is induced by the interaction of the first and second reporter molecules upon association of the first modified polypeptide with the second modified polypeptide; and correlating the measured characteristic with the presence or amount of analyte in the sample;

wherein the presence of the analyte promotes association of the first modified polypeptide with the second modified polypeptide.

7. The assay method of claim 6 wherein one of either the first or second modified polypeptides is attached to a solid support.

8. The assay method of claim 6 wherein the first reporter molecule is a first fluorochrome and the second reporter molecule is a second fluorochrome.

9. The assay method of claim 6 wherein the first reporter molecule is fluorescein or a derivative thereof and the second reporter molecule is rhodamine or a derivative thereof.

10. The assay method of claim 6 wherein the first reporter molecule is rhodamine or a derivative thereof and the second reporter molecule is fluorescein or a derivative thereof.

* * * * *